United States Patent [19]

Frickel et al.

[11] Patent Number: 5,073,563

[45] Date of Patent: Dec. 17, 1991

[54] ALKOXYCOUMARINS SUBSTITUTED BY A HETEROCYCLIC RADICAL, THEIR PREPARATION AND THERAPEUTIC AGENTS CONTAINING THESE COMPOUNDS

[75] Inventors: Fritz-Frieder Frickel, Mountain Lakes, N.J.; Thomas Kuekenhoehner, Frankenthal, Fed. Rep. of Germany; Beatrice Rendenbach-Mueller, Waldsee, Fed. Rep. of Germany; Harald Weifenbach, Ludwigshafen, Fed. Rep. of Germany; Hans-Juergen Teschendorf, Dudenhofen, Fed. Rep. of Germany

[73] Assignee: BASF Aktiengesellschaft, Ludwigshafen, Fed. Rep. of Germany

[21] Appl. No.: 417,451

[22] Filed: Oct. 5, 1989

[30] Foreign Application Priority Data

Oct. 13, 1988 [DE] Fed. Rep. of Germany ....... 3834860

[51] Int. Cl.$^5$ ................. C07D 417/12; A61K 31/425
[52] U.S. Cl. ..................................... 514/365; 546/174; 546/196; 546/269; 548/127; 548/131; 548/136; 548/143; 548/204; 548/214; 548/235; 548/240; 548/247; 548/248; 548/266.4; 548/327; 548/336; 548/374; 549/60; 549/289
[58] Field of Search .................. 548/204; 514/365

[56] References Cited

U.S. PATENT DOCUMENTS 4,701,456 10/1987 Dewald ............................... 514/253

FOREIGN PATENT DOCUMENTS 258228 7/1986 Fed. Rep. of Germany .
6457M 11/1988 France .

OTHER PUBLICATIONS

Ramesh, Syn. Comm. 16 1523 (1986).
Synthesis of 3-Phenyl-5-Aryoxymethylisoxazoles & Their UV Spectra & Physiological Activity, Krishna Murthy, et al., Indian Journal of Chemistry, vol. 10, pp. 38-40 (1972).
Chemical Abstracts, Band 90 No. 19, Husain, Mohamed Imtiaz et al. May 1979.
Chemical Abstracts, Band 99, No. 21 Nov. 1983, Stacchino, C. et al.
Chemical Abstracts, Band vol. 77, No. 5, Jul. 1972, Murthy, A et al.
Chemical Abstracts, Band vol. 102, No. 9, Mar., 1985, Kulshrestha, S. K. et al.

Primary Examiner—Robert Gerstl

Attorney, Agent, or Firm—Oblon, Spivak, McClelland, Maier & Neustadt

[57] ABSTRACT

An alkoxycoumarin substituted by a heterocyclic radical, of the formula

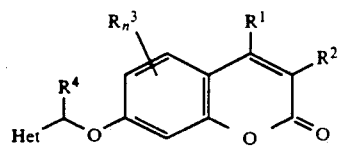

I

Het is one of the following heterocyclic radicals:

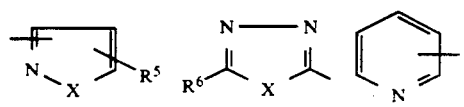

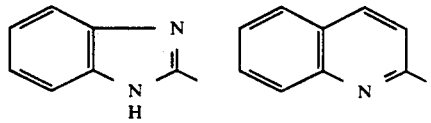

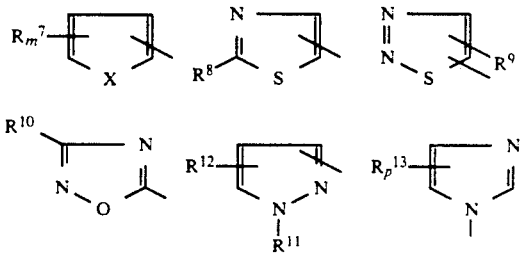

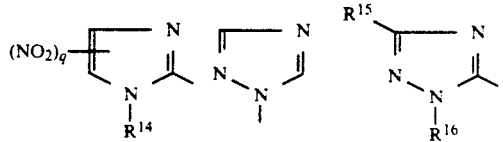

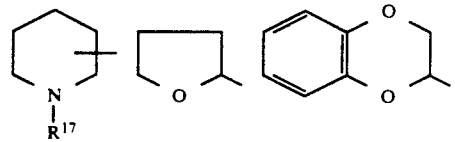

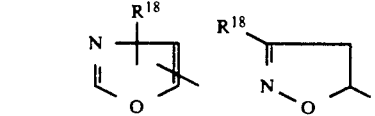

where X is oxygen or sulfur.

7 Claims, No Drawings

ALKOXYCOUMARINS SUBSTITUTED BY A HETEROCYCLIC RADICAL, THEIR PREPARATION AND THERAPEUTIC AGENTS CONTAINING THESE COMPOUNDS

The present invention relates to novel alkoxycoumarins substituted by a heterocyclic radical of the general formula I, their preparation and therapeutic agents which contain these compounds and two known compounds as the active ingredient, in particular for the treatment of disorders of the central nervous system.

Krishna Murthy et al., Indian J. Chem. 10 (1972), 34–40 have tested 4-methyl-7-(3-phenylisoxazol-5-yl-methoxy)-coumarin for fungicidal and bacteriostatic action with little or no success. Apart from this compound, the class of compounds described here is novel, as is the therapeutic use of the novel compound.

It is an object of the present invention to provide novel therapeutic agents, in particular for the treatment of disorders of the central nervous system.

We have found that this object is achieved by the novel compounds of the general formula I as claimed in claim 1, the preparation process as claimed in claim 2 and the therapeutic agents as claimed in claims 3 and 4.

In the general formula I

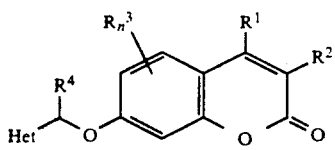

$R^1$ and $R^2$ may be identical or different and are each hydrogen, $C_1-C_5$-alkyl, $CF_3$, phenyl or halogen, or $R^1$ or $R^2$ together may form a common chain of 3 to 5 carbon atoms, $R^3$ is $C_1-C_5$-alkyl or halogen, n is an integer of from 0 to 3, $R^4$ is hydrogen or $C_1-C_4$-alkyl and Het is one of the following heterocyclic radicals:

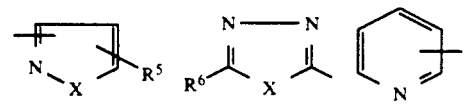

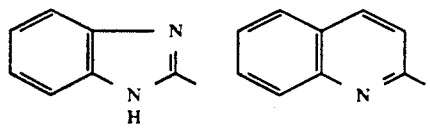

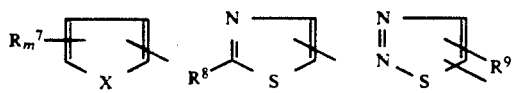

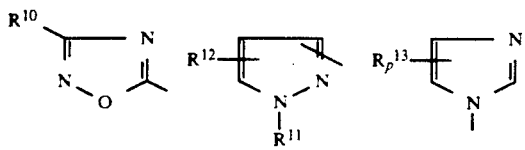

-continued

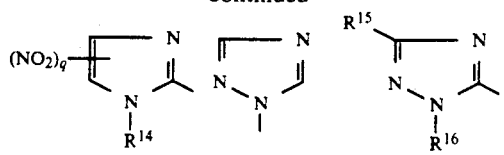

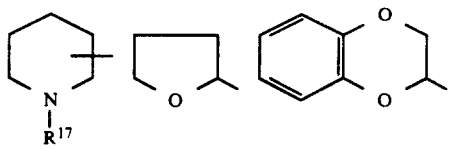

where X is oxygen or sulfur, $R^5$ is unsubstituted or $C_1-C_4$-alkoxy-substituted $C_1-C_{10}$-alkyl, 5-membered or 6-membered oxacycloalkyl, $C_3-C_7$-cycloalkyl, benzyl, phenyl which is unsubstituted or substituted by halogen or $NO_2$, a pyridine ring, $C_1-C_{15}$-alkoxycarbonyl or perfluoro-$C_1-C_2$-alkyl, $R^6$ is $C_1-C_5$-alkyl or $C_1-C_5$-alkoxy, $R^7$ is $C_1-C_5$-alkyl, unsubstituted or halogen-substituted benzyl or halogen, m is from 0 to 2, $R^8$ is $C_1-C_5$-alkyl, $C_3-C_6$-cycloalkyl, benzyl or phenyl, $R^9$ is hydrogen or $C_1-C_5$-alkyl, $R^{10}$ is $C_1-C_5$-alkyl or $C_1-C_6$-cycloalkyl, $R^{11}$ is $C_1-C_5$-alkyl, $R^{12}$ is hydrogen, $C_1-C_5$-alkyl or $C_3-C_6$-cycloalkyl, $R^{13}$ is $C_1-C_5$-alkyl or halogen, p is from 0 to 2, $R^{14}$ is $C_1-C_5$-alkyl, q is 0 or 1, $R^{15}$ and $R^{16}$ are each hydrogen, $C_1-C_5$-alkyl or benzyl, $R^{17}$ is hydrogen or $C_1-C_5$-alkyl and $R^{18}$ is $C_1-C_5$-alkyl, with the proviso that $R^5$ is not phenyl when X is oxygen, $R^1$ is methyl and $R^2$ to $R^4$ are each hydrogen.

Halogen is preferably chlorine or bromine.

The compounds of the general formula I can be prepared, for example, by reacting a hydroxycoumarin of the formula II

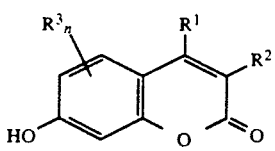

where $R^1$, $R^2$, $R^3$ and n have the abovementioned meanings, in a conventional manner with a compound of the formula III

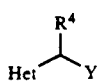

where $R^4$ and Het are as defined at the outset and Y is a nucleofugic leaving group, such as chlorine, bromine or $R^6SO_2O$. In this formula, $R^6$ is lower alkyl or is phenyl which is unsubstituted or substituted by $C_1-C_3$-alkyl or halogen. The reaction can be carried out, for example as described in Houben-Weyl, Georg Thieme-Verlag, Stuttgart 1965, Vol. 6/3, page 54 et seq., by heating the two components, preferably in the presence of an inert solvent such as benzene, toluene, methylene chloride, acetone, a lower alcohol, dimethylformamide or water. The reaction temperatures are advantageously from room temperature to the boiling point of the solvent used. The acid liberated is in general trapped by adding a base, such as alkali metal or alkaline earth metal hydroxide or carbonate or an amine, such as pyridine or triethylamine. Instead of the hydroxycoumarins of the formula II, it is also possible to react their alkali metal salts with the compounds of the formula III, preferably under anhydrous conditions in an aprotic solvent, such as ether, tetrahydrofuran, dimethylformamide, dimethoxyethane or dimethyl sulfoxide. The bases used in these cases are alkali metal hydrides or alkali metal alcoholates. Isolation and purification of the products are carried out by conventional methods, for example by recrystallization form a solvent, by column chromatography or if necessary by conversion into an acid addition compound where Het is basic.

The hydroxycoumarins II can be prepared by known methods, as described in, for example, Elderfield R. C., Heterocyclic Compounds, John Wiley Publishers, New York 1951, Vol. 2, page 174 et seq., for example by condensation of a dihydroxybenzene of the formula IV

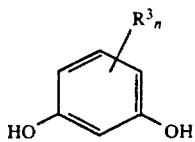

where $R^3$ and n have the abovementioned meanings, with a β-ketocarboxylic ester of the formula V

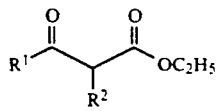

where $R^1$ and $R^2$ have the abovementioned meanings, in the presence of a condensing agent, such as sulfuric acid, phosphoric pentoxide or aluminum chloride.

The heterocyclic derivatives of the general formula III are either known and some of them are commercially available, or they can be prepared by generally known chemical processes. Methods for synthesizing thiophene derivatives are described in, for example, Comprehensive Heterocyclic Chemistry, R. Katritzky and W. Rees, Vol. 4, page 863 et seq., Pergamon Press 1984; furan derivatives in, for example, AU 579 693, U.S. Ser. No. 06/940649 or Advances in Heterocyclic Chemistry, 30 (1982), 167 et seq.; thiazole derivatives, oxazole derivatives, isothiazole derivatives, thiadiazole derivatives and oxidiazole derivatives in, for example, Comprehensive heterocyclic Chemistry, P. Katritzky and W. Rees, Vol. 6, pages 166, 177, 235, 386 and 425 et seq., Pergamon Press, 1984; imidazole derivatives in, for example, Advances in Heterocyclic Chemistry, 27 (1980), 242 et seq.; pyrazole derivatives in, for example, Heteroaromatic Nitrogen Compounds, The Azoles, page 31 et seq., Cambridge University Press, 1976; thiazole derivatives in, for example, Comprehensive Heterocyclic Chemistry, R. Katritzky and W. Rees, Vol. 5, page 733 et seq., Pergamon Press, 1984, and isoxazole derivatives in, for example, GB 1 560 711 and DE-A-2 754 832.

If the compounds of the general formula I are basic, they can be converted into the acid addition salts of a physiologically tolerated acid. Examples of conventional physiologically tolerated organic or inorganic acids are hydrochloric acid, hydrobromic acid, phosphoric acid, sulfuric acid, maleic acid, fumaric acid, lactic acid, tartaric acid, adipic acid and benzoic acid. Further acids are described in Fortschritte der Arzneimittelforschung, Vol. 10, page 224 et seq., Birkhäuser Verlag, Basle and Stuttgart, 1966.

The acid addition salts are, as a rule, obtained in a conventional manner by mixing the free base or a solution thereof with the corresponding acid or a solution thereof in an organic solvent, for example a lower alcohol, such as methanol ethanol or propanol, or an ether, such as diethyl or methyl tert-butyl ether. To improve deposition of crystals, it is also possible to use a mixture of the stated solvents. If necessary, pharmaceutically tolerated aqueous solutions of acid addition compounds of the novel compounds I can also be prepared by dissolving the free bases in an aqueous acid solution.

The compounds of the general formula I have monoaminooxidase (MAO)-inhibiting activity. Because of this, they can be used for the treatment of disorders of the central nervous system, in particular neurodegenerative disorders, and Parkinson's disease.

The MAO-inhibiting activity of the novel compounds can be determined using standard methods. For example, the determination of monoaminooxidases A and B were determined in dilute rat brain homogenate to which 1. different concentrations of the test substances and 2. $^{14}$C-phenylethylamine or $^{14}$C-tryptamine in a concentration of 0.4 μmol/l had been added. The mixture was incubated for 20 minutes at 37° C.

The reaction was then stopped by means of 0.1 normal HCl and the reaction products were determined, after extraction, in a toluene scintillator (PPO+POPOP in toluene). The blank value was determined in similar mixtures with an incubation time of t=0 min.

From the inhibitory values determined at the various inhibitor concentrations against a control, the mean inhibitory concentration (IC50) was calculated by linear regression following logit-log transformation.

The activity of some novel compounds determined in this manner is shown in the Table below:

| Ex. | IC$_{50}$ [μmol/l] | | MAO A / MAO B |
|---|---|---|---|
| | MAO A | MAO B | |
| 1 | 5.6 | 0.015 | 370 |
| 2 | 3.6 | 0.003 | 1200 |
| 3 | 1.5 | 0.0021 | 710 |
| 4 | ~10 | 0.0017 | ~5900 |
| 6 | ~10 | 0.0046 | ~2200 |
| 7 | ~10 | 0.011 | ~900 |
| 10 | >10 | 0.0022 | >4500 |
| 13 | >10 | 0.015 | >667 |
| 21 | ~10 | 0.0077 | ~1300 |
| 22 | >10 | 0.0016 | >6250 |
| 24 | ~10 | 0.003 | ~3300 |
| 25 | >10 | 0.017 | >590 |
| 26 | >10 | 0.0013 | >7700 |
| 29 | >10 | 0.0022 | >4500 |
| 30 | >10 | 0.0057 | >1700 |
| 32 | >10 | 0.0071 | >1400 |
| 33 | ~6 | 0.00073 | ~8200 |
| 34 | ~10 | 0.0022 | ~4500 |
| 35 | >10 | 0.00092 | >11000 |
| 42 | 0.35 | 0.00051 | 680 |
| 44 | ~7 | 0.0012 | ~5800 |
| 45 | 0.23 | 0.00051 | 450 |
| 50 | ~4 | 0.0043 | ~930 |
| 51 | >10 | 0.0008 | >12500 |
| 54 | >10 | 0.0015 | >6700 |
| 55 | >10 | 0.01 | >1000 |
| 58 | ~7 | 0.00084 | ~8300 |

-continued

| Ex. | IC$_{50}$ [μmol/l] MAO A | MAO B | MAO A / MAO B |
| --- | --- | --- | --- |
| 61 | >10 | 0.0019 | >1100 |
| 62 | >10 | 0.0075 | >1300 |
| 67 | >10 | 0.0011 | >9100 |
| 68 | >10 | 0.00077 | >13000 |
| 70 | >10 | 0.013 | >770 |
| 72 | ~10 | 0.0049 | ~2000 |
| 73 | >10 | 0.014 | >700 |
| 74 | 3.2 | 0.0055 | 580 |
| 75 | ~10 | 0.0014 | ~7000 |
| 78 | >10 | 0.0013 | >7700 |
| 79 | 2.9 | 0.0012 | 2400 |
| 80 | ~10 | 0.0014 | ~7100 |
| 84 | >10 | 0.0091 | >1100 |
| 85 | >10 | 0.0069 | >1700 |
| 87 | >10 | 0.014 | >700 |
| 92 | >10 | ~0.01 | >1000 |
| 94 | ~10 | 0.0012 | ~8300 |
| 96 | ~20 | 0.00061 | ~32000 |
| 97 | ~5 | 0.0036 | ~1400 |
| 98 | >10 | 0.00092 | >11000 |
| 99 | >10 | 0.0082 | >1200 |
| 100 | >10 | 0.00074 | >13000 |
| 101 | >10 | 0.001 | >10000 |
| 103 | >10 | 0.0018 | >5500 |
| 108 | ~10 | 0.0009 | ~11000 |
| 109 | >10 | 0.00088 | >11000 |
| Deprenyl | 2.0 | 0.0078 | 256 |
| Ro 19-6327 | >10 | 0.022 | >450 |

The novel compounds can be administered in a conventional manner, orally or parenterally (subcutaneously, intraveneously, intramuscularly or intraperitoneally).

The dose depends on the age, condition and weight of the patient and on the route of administration. As a rule, the daily dose of active compound is from about 10 to 500 mg per patient per day in the case of oral administration and from about 1 to 50 mg per patient per day in the case of parenteral administration.

The novel compounds can be used in the conventional solid or liquid pharmaceutical forms, for example as tablets, film tablets, capsules, powders, granules, coated tablets, suppositories, solutions or sprays. These are prepared in a conventional manner and to do so the active ingredients ar mixed with the conventional pharmaceutical auxiliaries, such as table binders, fillers, preservatives, tablet disintegrants, flow regulators, plasticizers, wetting agents, dispersants, emulsifiers, solvents, retarding agents, antioxidants and/or propellants (cf. H. Sucker et al.: Pharmazeutische Technologie, Thieme-Verlag, Stuttgart, 1978). The administration forms thus obtained normally contain the active compound in a concentration of from 1 to 99% by weight.

EXAMPLE 1

3,4-Dimethyl-7-(2-methyl-1,3,4-oxadiazol-5-yl)-methoxycoumarin 5.0 g of 7-hydroxy-3,4-dimethylcoumarin in 20 ml of 0.9 g of NaH (80%) in 50 ml of dimethylformamide at room temperature. After 45 minutes, 3.5 g of 2-chloromethyl-5-methyl-1,3,4-oxadiazole, dissolved in 20 ml of dimethylformamide, were added and the mixture was stirred overnight at room temperature. The reaction solution was hydrolyzed with ice water, and the precipitated solid was filtered off under suction and recrystallized from methanol.

Yield: 4.28 g (57%), mp. 159° C. $C_{15}H_{14}N_2O_4$ (286). Calculated: 62.93 C 4.93 H 9.78 N 22.35 O. Found: 63.0 C 4.9 H 9.7 N 22.2 O.

EXAMPLE 2

3,4-Dimethyl-7-(2-methyl-1,3,4-thiadiazol-5-yl)-methoxycoumarin

A mixture of 5.0 g of 7-hydroxy-3,4-dimethylcoumarin, 3.9 g of 2-chloromethyl-5-methyl-1,3,4-thiadiazole, 3.5 g of $K_2CO_3$ and 100 ml of acetone was refluxed for 20 hours and evaporated down, and the residue was partitioned in $H_2O$/methylene chloride. After the undissolved constituents had been separated off, the organic phase was washed once with 1N NaOH and then with $H_2O$, dried over $Na_2SO_4$ and evaporated down, and the residue was recrystallized from methanol and dried.

Yield: 5.8 g (74%), mp. 150° C. $C_{15}H_{14}N_2O_3S$ (302). Calculated: 59.59 C 4.67 H 9.27 N 15.87 O 10.60 S. Found: 59.4 C 4.5 H 9.4 N 16.0 O 10.6 S.

The following were prepared similarly to Example 2:

EXAMPLE 3

3,4-Dimethyl-7-(3-methylisoxazol-5-yl)-methoxycoumarin

Yield: 43%; mp. 148°–150° C. (ethanol). $C_{16}H_{15}NO_4$ (285). Calculated: 67.36 C 5.30 H 4.91 N 22.43 O. Found: 67.2 C 5.4 H 5.1 N 22.3 O.

The following were prepared similarly to Example 1:

EXAMPLE 4

3,4-Dimethyl-7-(3-n-propylisoxazol-5-yl)-methoxycoumarin

Yield: 50%; mp. 94° C. (methanol). $C_{18}H_{19}NO_4$ (313). Calculated: 68.99 C 6.11 H 4.47 N 20.42 O. Found: 68.7 C 6.2 H 4.4 N 20.2 O.

EXAMPLE 5

3,4-dimethyl-7-(4-pyridinyl)-methoxycoumarin

Yield: 52%; mp. 171° C. (methanol). $C_{17}H_{15}NO_3$ (281). Calculated: 72.58 C 5.37 H 4.98 N 17.06 O. Found: 72.3 C 5.5 H 4.8 N 16.9 O.

EXAMPLE 6

7-(3-Methoxymethylisoxazol-5-yl)-methoxy-3,4-dimethylcoumarin

Yield: 70%; mp. 133° C. (methanol). $C_{17}H_{17}NO_5$ (315). Calculated: 64.75 C 5.43 H 4.44 N 25.37 O. Found: 64.7 C 5.5 H 4.2 N 25.0 O.

EXAMPLE 7

7-(2-Ethyl-1,3,4-oxadiazol-5-yl)-methoxy-3,4-dimethylcoumarin

Yield: 54%; mp. 118° C. (methanol). $C_{16}H_{16}N_2O_4$ (300). Calculated: 63.99 C 5.37 H 9.33 N 21.31 O. Found: 63.7 C 5.8 H 9.3 N 21.3 O.

EXAMPLE 8

3,4-Dimethyl-7-(2-pyridinyl)-methoxycoumarin

Yield: 76%; mp. 156° C. (methanol). $C_{17}H_{15}NO_3$ (281). Calculated: 72.58 C 5.37 H 4.98 N 17.06 O. Found: 72.4 C 5.5 H 5.0 N 16.9 O.

EXAMPLE 9

3,4-Dimethyl-7-(3-pyridinyl)-methoxycoumarin

Yield: 64%; mp. 154° C. (methanol). $C_{17}H_{15}NO_3$ (281). Calculated: 72.58 C 5.37 H 4.98 N 17.06 O. Found: 72.4 C 5.6 H 4.9 N 16.9 O.

EXAMPLE 10

3,6-Dichloro-4-methyl-7-(2-cyclopropylthiazol-4-yl)-methoxycoumarin

The procedure and working up were carried out similarly to Example 2. In addition, 0.1% of 18-crown-lb 6 was added to the reaction mixture.

Yield: 26%; mp. 182°-184° C. (methanol). $C_{17}H_{13}Cl_2NO_3S$ (382). Calculated: 53.41 C 3.43 H 18.55 Cl 3.66 N 12.56 O 8.39 S. Found: 53.0 C 3.5 H 19.0 Cl 3.6 N 12.4 O 8.1 S.

EXAMPLE 11

7-(2-Chlorothiophen-5-yl)-methoxy-3,4-dimethylcoumarin

Yield: 69%; mp. 152°-154° C. (methanol). $C_{16}H_{13}ClO_3S$ (321). Calculated: 59.91 C 4.08 H 11.05 N 14.96 O 10.00 S. Found: 59.4 C 4.2 H 11.0 N 14.8 O 10.0 S.

EXAMPLE 12

7-(2-Methyl-1,3,4-thiadiazol-5-yl)-methoxycoumarin

Yield: 64%; mp. 155° C. (methanol). $C_{13}H_{10}N_2O_3S$ (274). Calculated: 56.92 C 3.67 H 10.21 N 17.50 O 11.69 S. Found: 56.6 C 3.6 H 10.3 N 17.4 O 11.6 S.

EXAMPLE 13

3-Methyl-7-(2-methyl-1,3,4-thiadiazol-5-yl)-methoxycoumarin

Yield: 59%; mp. 177° C. (methanol). $C_{14}H_{12}N_2O_3S$ (288). Calculated: 58.32 C 4.19 H 9.72 N 16.65 O 11.12 S. Found: 58.1 C 4.3 H 9.6 N 16.7 O 11.3 S.

EXAMPLE 14

4-Methyl-7-(2-methyl-1,3,4-thiadiazol-5-yl)-methoxycoumarin

Yield: 56%; mp. 143°-144° C. (methanol). $C_{14}H_{12}N_2O_3S$ (288). Calculated: 58.32 C 4.20 H 9.72 N 16.65 O 11.12 S. Found: 58.4 C 4.4 H 9.6 N 16.5 O 10.9 S.

EXAMPLE 15

7-(Benzimidazol-2-yl)-methoxy-3,4-dimethylcoumarin

Yield: 20%/ mp. 271°-274° C. (methanol). $C_{19}H_{16}N_2O_3$ (320). Calculated: 71.24 C 5.03 H 8.74 N 14.98 O. Found: 70.8 C 5.3 H 8.6 N 15.2 O.

EXAMPLE 16

7-(Quinolin-2-yl)-methoxy-3,4-dimethylcoumarin

Yield: 66%; mp. 189°-190° C. (methanol). $C_{21}H_{17}NO_3$ (331). Calculated: 76.12 C 5.17 H 4.23 N 14.48 O. Found: 76.1 C 5.2 H 4.2 N 14.3 O.

EXAMPLE 17

3,4-Dimethyl-7-(1-methylpiperidin-3-yl)-methoxycoumarin

The reaction mixture was stirred for 12 hours at 120° C. The preparation and working up were carried out a described under Example 1.

Yield: 55%; mp. 126°-128° C. (methanol). $C_{18}H_{23}NO_3$ (301). Calculated: 71.73 C 7.69 H 4.65 N 15.93 O. Found: 71.8 C 7.8 H 4.5 N 15.8 O.

EXAMPLE 18

7-(Tetrahydrofuran-2-yl)-methoxy-3,4-dimethylcoumarin

The reaction mixture was stirred for 12 hours at 120° C. The preparation and working up were carried out as described under Example 1.

Yield: 55%; mp. 151°-153° C. (methanol). $C_{16}H_{18}O_4$ (274). Calculated: 70.06 C 6.61 H 23.33 O. Found: 70.1 C 6.7 H 23.2 O.

EXAMPLE 19

7-[3-(3,4-Dichlorophenyl)-isoxazol-5yl-9-methoxy-3,4-dimethylcoumarin

Yield: 56%; mp. 225° C. $C_{21}H_{15}Cl_2NO_4$ (416). Calculated: 60.59 C 3.63 H 17.03 Cl 3.36 N 15.37 O. Found: 60.2 C 3.8 H 17.2 Cl 3.3 N 15.4 O.

EXAMPLE 20

3,4-Dimethyl-7-[3-(3-nitrophenyl)-isoxazol-5-yl)-methoxycoumarin

Yield: 20%; mp. 212°-219° C. (decomposition). $C_{21}H_{16}N_2O_2$ (392). Calculated: 64.28 C 4.11 H 7.14 N 24.47 O. Found: 63.8 C 4.5 H 6.9 N 24.0 O.

EXAMPLE 21

7-(Benzodioxan-2-yl)-methoxy-3,4-dimethylcoumarin

The reaction mixture was stirred for 12 hours at 120° C. The preparation and working up were carried out as described under Example 1.

Yield: 53%; mp. 145° C. (ethanol). $C_{20}H_{18}O_5$ (338). Calculated: 71.0 C 5.36 H 23.64 O. Found: 70.8 C 5.4 H 23.4 O.

EXAMPLE 22

7-(2-Benzylfuran-4-yl)-methoxy-3,4-dimethylcoumarin

Yield: 68%; mp. 113° C. (methanol). $C_{23}H_{20}O_4$ (360). Calculated: 76.65 C 5.59 H 17.76 O. Found: 76.4 C 5.6 H 17.7 O.

EXAMPLE 23

7-(2-Methyl-1,3,4-thiadiazol-5-yl)-methoxy-4-phenylcoumarin

The reaction mixture was stirred for 3 hours at 100° C. and overnight at room temperature. The preparation and working up were carried out as described under Example 1.

Yield: 80%; mp. 166°-167° C. (methanol). $C_{19}H_{14}N_2O_3S$ (350). Calculated: 65.13 C 4.03 H 7.99 N 13.70 O 9.15 S. Found: 65.3 C 4.1 H 8.0 N 13.9 O 9.1 S.

EXAMPLE 24

3,4-Dimethyl-7-(2-methylthiazol-4-yl)-methoxycoumarin

Yield: 69%; mp. 149°–150° C. (methanol). $C_{16}H_{15}NO_3S$ (301). Calculated: 63.77 C 5.02 H 4.65 N 15.93 O 10.64 S. Found: 63.5 C 5.1 H 4.6 N 16.1 O 10.4 S.

EXAMPLE 25

7-[2-(3-Chlorobenzyl)-furan-4-yl]-methoxy-3,4-dimethylcoumarin

Yield: 45%; mp. 115° C. (methanol). $C_{23}H_{19}ClO_4$ (395). Calculated: 69.96 C 4.85 H 8.98 Cl 16.21 O. Found: 69.9 C 5.1 H 8.8 Cl 16.5 O.

EXAMPLE 26

7-(3-Iospropyl-1,2,4-oxadiazol-5-yl)-methoxy-3,4-dimethylcoumarin

Yield: 82%; mp. 142° C. (methanol). $C_{17}H_{18}N_2O_4$ (314). Calculated: 64.96 C 5.77 H 8.91 N 20.36 O. Found: 64.8 C 5.9 H 8.9 N 20.4 O.

EXAMPLE 27

3,4-Dimethyl-7-[3-(tetrahydropyran-4-yl)-isoxazol-5-yl]-methoxycoumarin

Yield: 77%; mp. 151° C. (methanol). $C_{20}H_{21}NO_5$ (355). Calculated: 67.59 C 5.96 H 3.94 N 22.51 O. Found: 67.5 C 5.9 H 4.0 N 22.5 O.

EXAMPLE 28

7-(4,5-Dihydro-3-propylisoxazol-5-yl)-methoxy-3,4-dimethylcoumarin

The reaction mixture was stirred for 8 hours at 100° C. The preparation and working up were carried out as described under Example 1.

Yield: 60%; mp. 147° C. (methanol). $C_{18}H_{21}NO_4$ (315). Calculated: 68.55 C 6.71 H 4.44 N 20.29 O. Found: 68.3 C 6.7 H 4.3 N 20.0 O.

EXAMPLE 29

7-(5-Isopropyl-1-methylpyrazol-3-yl)-methoxy-3,4-dimethylcoumarin

Yield: 43%; mp. 113° C. (methanol). $C_{19}H_{22}N_2O_3$ (326). Calculated: 69.92 C 6.79 H 8.58 N 14.71 O. Found: 69.5 C 6.9 H 8.4 N 14.6 O.

EXAMPLE 30

3-Chloro-4-methyl-7-(2-methyl-1,3,4-thiadiazol-5-yl)-methoxycoumarin

Yield: 62%; mp. 176°–177° C. (methanol). $C_{14}H_{11}ClN_2O_3S$ (323). Calculated: 52.10 C 3.44 H 10.98 Cl 8.68 N 14.87 O 9.93 S. Found: 52.2 C 3.6 H 10.8 Cl 8.7 N 15.2 O 9.2 S.

EXAMPLE 31

3-Ethyl-4-methyl-7-(2-methyl-1,3,4-thiadiazol-5-yl)-methoxycoumarin

Yield: 78%; mp. 167° C. (methanol). $C_{16}H_{16}N_2O_3S$ (316). Calculated: 60.74 C 5.10 H 8.85 N 15.17 O 10.13 S. Found: 60.6 C 5.2 H 9.0 N 15.1 O 10.1 S.

EXAMPLE 32

3,4-Tetramethylen-7-(2-methyl-1,3,4-thiadiazol-5-yl)-methoxycoumarin

Yield: 81%; mp. 172°–174° C. (methanol). $C_{17}H_{16}N_2O_3S$ (338). Calculated: 62.18 C 4.91 H 8.53 N 14.62 O 9.76 S. Found: 61.8 C 5.1 H 8.7 N 14.8 O 9.7 S.

EXAMPLE 33

7-(3-Isopropylisoxazol-5-yl)-methoxy-3,4-dimethylcoumarin

Yield: 62%; mp. 105° C. (methanol). $C_{18}H_{19}NO_4$ (313). Calculated: 69.00 C 6.11 H 4.47 N 20.42 O. Found: 68.8 C 6.3 H 4.4 N 20.4 O.

EXAMPLE 34

7-(3-Isobutylisoxazol-5-yl)-methoxy-3,4-dimethylcoumarin

Yield: 79%; mp. 86° C. (methanol). $C_{19}H_{21}NO_4$ (327). Calculated: 69.71 C 6.47 H 4.28 N 19.55 O. Found: 69.7 C 6.7 H 4.3 N 19.5 O.

EXAMPLE 35

7-(3-tert-Butylisoxazol-5-yl)-methoxy-3,4-dimethylcoumarin

Yield: 58%; mp. 121° C. (methanol). $C_{19}H_{21}NO_4$ (327). Calculated: 69.71 C 6.47 H 4.28 N 19.55 O. Found: 69.7 C 6.7 H 4.3 N 19.4 O.

EXAMPLE 36

7-(3-Ethoxycarbonylisoxazol-5-yl)-methoxy-3,4-dimethylcoumarin

Yield: 71%; mp. 202° C. (methylene chloride/ethyl acetate). $C_{18}H_{17}NO_6$ (343). Calculated: 62.97 C 4.99 H 4.08 N 27.96 O. Found: 62.7 C 5.1 H 4.0 N 27.8 O.

EXAMPLE 37

7-(4,5-Dichloroimidazol-1-yl)-methoxy-3,4-dimethylcoumarin

Yield: 84%; mp. 235° C. (methylene chloride/ethyl acetate). $C_{15}H_{12}Cl_2N_2O_3$ (339). Calculated: 53.12 C 3.57 H 20.91 Cl 8.26 N 14.15 O. Found: 52.2 C 3.6 H 20.6 Cl 8.0 N 14.2 O.

EXAMPLE 38

3,4-Dimethyl-7-(1,2,4-triazol-1-yl)-methoxycoumarin

Yield: 73%; mp. 223°–225° C. (methanol). $C_{14}H_{13}N_2O_3$ (271). Calculated: 61.99 C 4.83 H 15.49 N 17.69 O. Found: 61.8 C 5.0 H 15.6 N 17.5 O.

EXAMPLE 39

3,4-Dimethyl-7-(4,5-dimethylimidazol-1-yl)-methoxycoumarin

Yield: 37%; mp. 196°–198° C. (ethyl acetate). $C_{17}H_{18}N_2O_3$ (298). Calculated: 68.44 C 6.08 H 9.39 N 16.09 O. Found: 68.1 C 6.2 H 9.4 N 16.0 O.

EXAMPLE 40

3,4-Dimethyl-7-(thiophen-2-yl)-methoxycoumarin

Yield: 43%; mp. 169°–172° C. (methanol). $C_{16}H_{14}O_3S$ (286). Calculated: 67.11 C 4.93 H 16.76 O 11.20 S. Found: 67.0 C 5.0 H 16.8 O 11.2 S.

EXAMPLE 41

3,4-Dimethyl-7-(thiophen-3-yl)-methoxycoumarin

Yield: 41%; mp. 158°–160° C. (methanol). $C_{15}H_{14}O_3S$ (286). Calculated: 67.11 C 4.93 H 16.76 O 11.20 S. Found: 66.9 C 5.1 H 16.8 O 11.1 S.

EXAMPLE 42

3,4-Dimethyl-7-(2-methylthiophen-5-yl)-methoxycoumarin

Yield: 66%; mp. 123°–126° C. (methanol). $C_{17}H_{16}O_3S$ (300). Calculated: 67.98 C 5.37 H 15.98 O 10.67 S. Found: 67.8 C 5.5 H 15.9 O 10.7 S.

EXAMPLE 43

7-(2-Chlorothiphen-4-yl)-methoxy-3,4-dimethylcoumarin

Yield: 53%; mp. 137°–139° C. (methanol). $C_{16}H_{13}ClO_3s$ (321). Calculated: 59.91 C 4.08 H 11.05 Cl 14.96 O 10.0 S. Found: 59.6 C 4.1 H 11.0 Cl 15.1 O 9.9 S.

EXAMPLE 44

3,4-Dimethyl-7-(3-cyclopropyl-1,2,4-oxadiazol-5-yl)-methoxycoumarin

Yield: 41%; mp. 128°–131° C. (methanol). $C_{17}H_{16}N_2O_4$ (312). Calculated: 65.38 C 5.16 H 8.97 N 20.49 O. Found: 65.1 C 5.2 H 9.0 N 20.6 O.

EXAMPLE 45

3,4-Dimethyl-7-(3-methylthiophen-2-yl)-methoxycoumarin

Yield: 52%; mp. 147° C. (methanol). $C_{17}H_{16}O_3S$ (300). Calculated: 67.98 C 5.37 H 15.98 O 10.67 S. Found: 68.0 C 5.4 H 15.9 O 10.7 S.

EXAMPLE 46

7-(2-Bromothiophen-5-yl)-methoxy-3,4-dimethylcoumarin

Yield: 65%; mp. 140°–143° C. (ethyl acetate). $C_{16}H_{13}BrO_3S$ (365). Calculated: 52.62 C 3.59 H 21.88 Br 13.14 O 8.78 S. Found: 52.7 C 3.9 H 21.7 Br 13.3 O 8.8 S.

EXAMPLE 47

7-(2-Bromothiophen-4yl)-methoxy-3,4-dimethylcoumarin

Yield: 67%; mp. 104° C. (ethanol). $C_{16}H_{13}BrO_3S$ (365). Calculated: 52.62 C 3.59 H 21.88 Br 13.14 O 8.78 S. Found: 52.7 C 3.7 H 21.4 Br 13.4 O 8.8 S.

EXAMPLE 48

7-(4-Bromothiophen-2-yl)-methoxy-3,4-dimethylcoumarin

Yield: 53%; mp. 131°–134° C. (methanol). $C_{16}H_{13}BrO_3S$ (365). Calculated: 52.62 C 3.59 H 21.88 Br 13.14 O 8.78 S. Found: 52.3 C 3.7 H 21.5 Br 13.3 O 8.7 S.

EXAMPLE 49

7-(2.3-Dibromothiophen-4-yl)-methoxy-3,4-dimethylcoumarin

Yield: 57%; mp. 194°–196° C. (methanol). $C_{16}H_{12}Br_2O_3S$ (444). Calculated: 43.27 C 2.72 H 35.8 Br 10.81 O 7.22 s. Found: 43.2 C 2.7 H 35.9 Br 11.1 O 7.1 S.

EXAMPLE 50

3,4-Dimethyl-7-(3-methyl-1,2,4-oxadiazol-5-yl)-methoxycoumarin

Yield: 63%; mp. 172°–174° C. (methanol). $C_{15}H_{14}N_2O_4$(286). Calculated: 62.93 C 4.89 H 9.79 N 22.37 O. Found: 62.6 C 5.0 H 9.8 N 22.9 O.

EXAMPLE 51

7-(3-Cyclopropylisoxazol-5-yl)-methoxy-3,4-dimethylcoumarin

Yield: 36%; mp. 158°–160° C. (methanol). $C_{18}H_{17}NO_4$ (311). Calculated: 69.44 C 5.50 H 4.50 N 20.56 O. Found: 69.0 C 5.6 H 4.5 N 21.2 O.

EXAMPLE 52

3,4-dimethyl-7-(3-methylisothiazol-4-yl)-methoxycoumarin

Yield: 28%; mp. 163°–165° C. (methanol). $C_{16}H_{15}NO_3S$ (301). Calculated: 63.77 C 5.02 H 4.65 N 15.93 O 10.65 S. Found: 63.9 C 5.1 H 4.7 N 15.5 O 10.5 S.

EXAMPLE 53

3,4-Dimethyl-7-(1,2,3-thiadiazol-4-yl)-methoxycoumarin

Yield: 39%; mp. 171°–173° C. (methanol). $C_{14}H_{12}N_2O_3S$ (288). Calculated: 56.51 C 4.38 H 10.14 N 17.37 O 11.6 S. Found: 56.9 C 4.1 H 9.6 N 17.7 O 11.8 S.

EXAMPLE 54

3-Chloro-7-(5-isopropyl-1-methylpyrazol-3yl)-methoxy-4-methylcoumarin

The reaction was carried out as described under Example 1. After the hydrolysis, extraction was carried out with methylene chloride, the organic phase was washed with $H_2O$, dried over $Na_2SO_4$ and evaporated down and the residue was recrystallized from methanol.

Yield: 33%; mp. 162°–165° C. $C_{18}H_{19}ClN_2O_3$ (346.5). Calculated: 62.34 C 5.52 H 8.08 N 13.84 O 10.22 S. Found: 62.3 C 5.8 H 8.1 N 13.7 O 9.7 S.

EXAMPLE 55

7-(5-Isopropyl-1-methylpyrazol-3-yl)-methoxy-3,4-tetramethylenecoumarin

Yield: 29%; mp. 138°–140° C. (methanol). $C_{21}H_{24}N_2O_3$ (352). Calculated: 71.57 C 6.86 H 7.95 N 13.62 O. Found: 71.0 C 6.9 H 8.0 N 14.1 O.

EXAMPLE 56

4-Ethyl-3-methyl-7-(2-methyl-1,3,4-thiadiazol-5-yl)-methoxycoumarin

Yield: 24%; mp. 135°–138° C. (methanol). $C_{16}H_{16}N_2O_3S$ (316). Calculated: 60.74 C 5.10 H 8.85 N 15.17 O 10.13 S. Found: 61.0 C 5.5 H 8.5 N 15.0 O 9.8 S.

EXAMPLE 57

3,4-Dimethyl-7-(4-methyl-1,2,3-thiadiazol-5-yl)-methoxycoumarin

Yield: 29%; mp. 204°–206° C. (methanol). $C_{15}H_{14}N_2O_3S$ (302). Calculated: 59.60 C 4.63 H 9.27 N 15.89 O 10.59 S. Found: 59.3 C 4.8 H 9.3 N 15.9 O 10.7 S.

EXAMPLE 58

7-(5-Cyclopropylisoxazol-3-yl)-methoxy-3,4-dimethylcoumarin

Yield: 67%; mp. 107°–109° C. (methanol). $C_{18}H_{17}NO_4$ (311). Calculated: 69.44 C 5.50 H 4.50 N 20.56 O. Found: 69.1 C 5.8 H 4.3 N 20.4 O.

EXAMPLE 59

7-(3-Trifluoromethylisoxazol-5-yl)-methoxy-3,4-dimethylcoumarin

Yield: 47%; mp. 180°–182° C. (methanol). $C_{16}H_{12}F_3NO_4$ (339). Calculated: 56.64 C 3.57 H 16.80 F 4.13 N 18.86 O. Found: 56.6 C 3.7 H 16.8 F 4.0 N 18.9 O.

EXAMPLE 60

3,4-Dimethyl-7-(1-methylimidazol-2-yl)-methoxycoumarin

The procedure and working up were carried out as described under Example 54.

Yield: 28%; mp. 182°–185° C. $C_{16}H_{16}N_2O_3$ (284). Calculated: 67.59 C 5.67 H 9.85 N 16.88 O. Found: 67.2 C 6.0 H 9.7 N 16.5 O.

EXAMPLE 61

7-(5-Cyclopropyl-1-methylpyrazol-3-yl)-methoxy-3,4-dimethylcoumarin

Yield: 51%; mp. 124°–127° C. (methanol). $C_{19}H_{20}N_2O_3$ (324). Calculated: 70.35 C 6.21 H 8.64 N 14.80 O. Found: 70.1 C 6.4 H 8.7 N 14.6 O.

EXAMPLE 62

7-(2-Ethoxy-1,3,4-thiadiazol-5-yl)-methoxy-3,4-dimethylcoumarin

Yield: 37%; mp. 174°–176° C. (methanol). $C_{16}H_{16}N_2O_4S$ (332). Calculated: 57.82 C 4.85 H 8.43 N 19.25 O 9.65 S. Found: 58.3 C 5.3 H 8.1 N 18.9 O 9.4 S.

EXAMPLE 63

3,4-Dimethyl-7-(2-phenylthiazol-4-yl)-methoxycoumarin

The procedure and working up were carried out as described under Example 54.

Yield: 39%; mp. 152°–154° C. (methanol). $C_{21}H_{17}NO_3S$ (363). Calculated: 69.40 C 4.71 H 3.85 N 13.21 O 8.82 s. Found: 69.1 C 4.9 H 3.7 N 13.1 O 9.0 S.

EXAMPLE 64

4-Ethyl-7-(5-isopropyl-1methylpyrazol-3-yl)-methoxy-3-methylcoumarin

The procedure and working up were carried out as described under Example 54.

Yield: 33%; mp. 101°–103° C. $C_{20}H_{24}N_2O_3$ (340). Calculated: 70.57 C 7.11 H 8.23 N 14.10 O. Found: 70.2 C 7.5 H 8.3 N 13.7 O.

EXAMPLE 65

6-Chloro-3,4-dimethyl-7-(2-methyl-1,3,4-thiadiazol-5-yl)-methoxycoumarin

Yield: 37%; mp. 209°–210° C. (methanol). $C_{15}H_{13}ClN_2O_3S$ (336.5). Calculated: 53.49 C 3.89 H 10.53 Cl 8.32 N 14.25 O 9.52 S. Found: 53.3 C 3.9 H 10.5 Cl 8.2 N 14.1 O 9.6 S.

EXAMPLE 66

3,4-Dimethyl-7-(4-methylisothiazol-5-yl)-methoxycoumarin

Yield: 25; mp. 180° C. (methanol). $C_{16}H_{15}NO_3S$ (301). Calculated: 63.56 C 5.33 H 4.63 N 15.87 O 10.6 S. Found: 63.5 C 5.3 H 4.8 N 15.3 O 10.9 S.

EXAMPLE 67

6-Bromo-3,4-dimethyl-7-(2methyl-1,3,4-thiadiazol-5-yl)-methoxycoumarin

Yield: 36%; mp. 205° C. (methanol). $C_{15}H_{13}BrN_2O_3S$ (381). Calculated: 47.26 C 3.44 H 20.96 Br 7.35 N 12.59 O 8.41 S. Found: 47.1 C 3.5 H 20.8 Br 7.4 N 12.7 O 8.5 S.

EXAMPLE 68

7-(3-Cyclobutylisoxazol-5-yl)-methoxy-3,4-dimethylcoumarin

The procedure and working up were carried out as described under Example 54.

Yield: 26%; mp. 100°–101° C. (methanol). $C_{19}H_{19}NO_4$ (325). Calculated 70.15 C 5.84 H 4.3 N 19.7 O. Found: 69.9 C 5.9 H 4.6 N 19.5 O.

EXAMPLE 69

7-(1-Benzyl-1,2,4-triazol-5-yl)-methoxy-3,4-dimethylcoumarin

Yield: 49%; mp. 151°–152° C. (methanol). $C_{21}H_{19}N_3O_3$ (361) Calculated: 69.79 C 5.30 H 11.63 N 13.28 O. Found: 69.3 C 5.5 H 11.8 N 13.6 O.

EXAMPLE 70

7-(1-Isopropyl-1,2,4-triazol-5-yl)-methoxy-3,4-dimethylcoumarin hydrochloride

The procedure was carried out as described under Example 1. After the hydrolysis, extraction was effected with methylene chloride and the organic phase was evaporated down and the residue was purified by column chromatography (silica gel; 20:1 $CH_2Cl_2/CH_3OH$). The free base was dissolved in $CH_2Cl_2$ and HCl in ether was added. The precipitate formed was filtered off under suction, washed with a little ether and dried.

Yield: 32%; mp. 179°–181° C. $C_{17}H_{20}ClN_3O_3$ (350). Calculated: 58.37 C 5.76 H 10.13 Cl 12.01 N 13.71 O. Found: 57.9 C 5.9 H 10.0 Cl b 12.1 N 14.2 O.

EXAMPLE 71

3,4-Dimethyl-7-[1-(1,3-dimethyl-1,2,4-triazol-5yl)]-ethoxycoumarin

Yield: 32%; mp. 160°–162° C. (methanol). $C_{17}H_{19}N_3O_3$(313). Calculated: 65.16 C 6.11 H 13.41 N 15.32 O. Found: 65.1 C 6.2 H 13.3. N 15.6 O.

EXAMPLE 72

7-(3-Isopropyl-1-methylpyrazol-5-yl)-methoxy-3,4-dimethylcoumarin

Yield: 37%; mp. 125°–126° C. (methanol). $C_{19}H_{22}N_2O_3$ (326). Calculated: 69.92 C 6.79 H 8.58 N 14.71 O. Found: 69.3 C 7.1 H 9.1 N 14.3 O.

EXAMPLE 73

3,4-Dimethyl-7-(1,5-dimethylpyrazol-3-yl)-methoxycoumarin

Yield: 23%; mp. 169°–17° C. (methanol). $C_{17}H_{18}N_2O_3$ (298). Calculated: 68.44 C 6.08 H 9.39 N 16.09 O. Found: 68.2 C 6.3 H 9.1 N 16.3 O.

EXAMPLE 74

7-(2-Benzylthiazol-4-yl)-methoxy-3,4-dimethylcoumarin

Yield: 21%; mp. 142°–143° C. (methanol). $C_{22}H_9NO_3S$ (377). Calculated: 70.01 C 5.07 H 3.71 N 12.72 O 8.49 S. Found: 69.6 C 5.2 H 3.7 N 13.0 O 8.4 S.

EXAMPLE 75

7-(2-Isopropylthiazol-4-yl)-methoxy-3,4-dimethylcoumarin

Yield: 20%; mp. 103° C. (methanol). $C_{18}H_{19}NO_3S$ (329). Calculated: 65.63 C 5.81 H 4.25 N 14.57 O 9.79 S. Found: 65.0 C 6.0 H 3.9 N 15.2 O 9.2 S.

EXAMPLE 76

3,4,8-Trimethyl-7-(2-methyl-1,3,4-thiadiazol-5-yl)-methoxycoumarin

Yield: 62%; mp. 231°–233° C. (methanol). $C_{16}H_{16}N_2O_3S$ (316). Calculated: 60.74 C 5.10 H 8.85 N 15.17 O 10.13 S. Found: 60.5 C 5.2 H 9.0 N 15.1 O 10.3 S.

EXAMPLE 77

3,4,5-Trimethyl-7-(2-methyl-1,3,4-thiadiazol-5-yl)-methoxycoumarin

Yield: 76%; mp. 201°–203° C. (methanol). $C_{16}C_{16}N_2O_3S$ (316). Calculated 60.74 C 5.10 H 8.85 N 15.17 O 10.13 S. Found: 60.5 C 5.2 H 9.0 N 15.1 O 10.1 S.

EXAMPLE 78

7-(3-Cyclopentylisoxazol-5-yl)-methoxy-3,4-dimethylcoumarin

The procedure was carried out as described under Example 1. After the hydrolysis, the precipitated solid was filtered off under suction and extracted by boiling with 5 times 100 ml of n-heptane. The combined heptane phases were evaporated down and the residue was recrystallized with methanol.

Yield: 15%; mp. 81°–83° C. $C_{20}H_{21}NO_4$ (339). Calculated: 70.78 C 6.24 H 4.13 N 18.86 O. Found: 70.6 C 6.2 H 4.0 N 18.8 O.

EXAMPLE 79

7-[3-(1-Methoxyethyl)-isoxazol-5-yl]-methoxy-3,4-dimethylcoumarin

The reaction mixture was stirred for 12 hours at 70° C. The preparation and working up were carried out as described under Example 1.

Yield: 37%; mp. 124°–127° C. (methanol). $C_{18}H_{19}NO_5$ (329). Calculated: 65.64 C 5.81 H 4.25 N 24.29 O. Found: 65.4 C 6.0 H 4.2 N 24.7 O.

EXAMPLE 10

7-(2-Cyclopropylthiazol-4-yl)-methoxy-3,4-dimethylcoumarin

The reaction mixture was stirred for 12 hours at 70° C. The preparation and working up were carried out as described under Example 1.

Yield: 51%; mp. 151° C. (methanol). $C_{18}H_{17}NO_3S$ (327). Calculated: 66.03 C 5.23 H 4.28 N 14.66 O 9.79 S. Found: 65.7 C 5.4 H 4.4 N 15.0 O 9.7 S.

EXAMPLE 81

3,4-Dimethyl-7-(1-methylpyrazol-3-yl)-methoxycoumarin

Yield: 47%; mp. 135° C. (methanol). $C_{16}H_{16}N_2O_3$ (284). Calculated: 67.59 C 5.67 H 9.85 N 16.88 O. Found: 67.5 C 5.8 H 9.8 N 17.0 O.

EXAMPLE 82

7-(5-Isopropyl-1-methylpyrazol-3-yl)-methoxy-3,4,5-trimethylcoumarin

Yield: 65%; mp. 128° C. (methanol). $C_{20}H_{24}N_2O_3$ (340). Calculated: 70.57 C 7.11 H 8.23 N 14.10 O. Found: 70.3 C 7.1 H 8.1 N 14.5 O.

EXAMPLE 83

7-(5-Isopropyl-1-methylpyrazol-3-yl)-methoxy-3,4,8-trimethylcoumarin

Yield: 46%; mp. 146°–148° C. (methanol). $C_{20}H_{24}N_2O_3$ (340). Calculated: 70.57 C 7.11 H 8.23 N 14.10 O. Found: 70.3 C 7.1 H 8.1 N 14.5 O.

EXAMPLE 84

6-Ethyl-7-(5-isopropyl-1-methylpyrazol-3-yl)-methoxy-3,4-dimethylcoumarin

Yield: 51%; mp. 136°–137° C. (methanol). $C_{21}H_{26}N_2O_3$ (354). Calculated: 71.16 C 7.39 H 7.90 N 13.54 O. Found: 71.1 C 7.5 H 7.9 N 13.6 O.

EXAMPLE 85

6-Ethyl-3,4-dimethyl-7-(2-methyl-1,3,4-thiadiazol-5-yl)-methoxycoumarin

Yield: 80%; mp. 201°–203° C. (methanol). $C_{17}H_{18}N_2O_5$ (330). Calculated: 61.80 C 5.49 H 8.48 N 14.53 O 9.70 S. Found: 61.7 C 5.6 H 8.4 N 14.6 O 9.7 S.

EXAMPLE 86

3,4-Dimethyl-7-[3-(pyridin-2-yl)-isoxazol-5-yl]-methoxycoumarin

Yield: 86%; mp. 193° C. (methanol). $C_{20}H_{16}N_2O_4$ (348). Calculated: 68.96 C 4.63 H 8.04 N 18.37 O. Found: 68.4 C 4.6 H 8.1 N 17.9 O.

EXAMPLE 87

7-(3-Cyclohexylisoxazol-5-yl)-methoxy-3,4-dimethylcoumarin

The procedure and working up were carried out as described under Example 78.

Yield: 66%; mp. 122° C. (n-heptane). $C_{21}H_{23}NO_4$ (353). Calculated: 71.73 C 6.56 H 3.86 N 18.11 O. Found: 71.5 C 6.7 H 4.0 N 17.8 O.

EXAMPLE 88

7-(3-tert-Butyl-1-methylpyrazol-5yl)-methoxy-3,4-dimethylcoumarin

Yield: 28%; mp. 143° C. (methanol). $C_{20}H_{24}N_2O_3$ (340). Calculated: 70.57 C 7.11 H 8.23 N 14.10 O. Found: 70.4 C 7.3 H 8.1 N 13.8 O.

EXAMPLE 89

3,4-Dimethyl-7-(1,3-dimethyl-1,2,4-triazol-5-yl)-methoxycoumarin

Yield: 42%; mp. 180° C. (methanol). $C_{16}H_{17}N_3O_3$ (399). Calculated: 64.20 C 5.72 H 14.04 N 16.04 O. Found: 64.5 C 5.9 H 13.8 N 15.8 O.

EXAMPLE 90

3,4-Dimethyl-7-(1-methyl-5-nitroimidazol-2-yl)-methoxycoumarin

Yield: 22%; mp. 184° C. (acetone). $C_{16}H_{15}N_3O_5$ (329). Calculated: 58.36 C 4.59 H 12.76 N 24.5 O. Found: 58.0 C 4.7 H 12.6 N 24.5 O.

EXAMPLE 91

6-Bromo-3,4-dimethyl-7-(1-methyl-5-isopropylpyrazol-3-yl)-methoxycoumarin

Yield: 32%; mp. 177°–179° C. (methanol).

EXAMPLE 92

7-(2-tert-Butylthiophen-5-yl)-methoxy-3,4-dimethylcoumarin

Yield: 86%; mp. 137° C. (ethyl acetate). $C_{20}H_{22}O_3S$ (342). Calculated: 70.15 C 6.48 H 14.02 O 9.36 S. Found: 69.7 C 6.4 H 14.2 O 9.2 S.

EXAMPLE 93

6-Bromo-7-(2-tert-butylthiophen-5-yl)-methoxy-3,5-dimethylcoumarin

Yield: 4.5%; mp. 170° C. (methanol/ethyl acetate). $C_{20}H_{21}BrO_3S$ (421). Calculated: 50.01 C 5.02 H 18.96 Br 11.39 O 7.61 S. Found: 56.8 C 5.0 H 18.3 Br 11.5 O 7.7 S.

EXAMPLE 94

3,4-Dimethyl-7-(2-cyclopropyl-1,3,4-thiadiazol-5yl)-methoxycoumarin

Yield: 62%; mp. 143° C. (ethyl acetate). $C_{17}H_{16}N_2O_3S$ (328). Calculated: 62.18 C 4.91 H 8.53 N 14.62 O 9.68 S. Found: 61.7 C 4.9 H 8.5 N 14.6 O 10.0 S.

EXAMPLE 95

3,4-Dimethyl-7-(3,5-dimethylisoxazol-4-yl)-methoxycoumarin

Yield: 53%; mp. 145°–147° C. (methanol). $C_{17}H_{17}NO_4$ (299). Calculated: 68.22 C 5.72 H 4.68 N 21.38 O. Found: 67.9 C 5.9 H 4.5 N 21.8 O.

EXAMPLE 96

3,4-Dimethyl-7-[3-(1-methylcyclopropyl)-isoxazol-5yl]-9-methoxycoumarin

Yield: 64%; mp. 122° C. (methanol). $C_{19}H_{19}NO_4$ (325). Calculated: 70.14 C 5.89 H 4.31 N 19.69 O. Found: 69.8 C 5.9 H 4.3 N 19.8 O.

EXAMPLE 97

3,4-Dimethyl-7-[3-(tetrahydrofuran-3-yl)-isoxazol-5-yl]-methoxycoumarin

Yield: 48%; mp. 122° C. (methanol). $C_{20}H_{19}NO_5$ (325). Calculated: 66.85 C 5.61 H 4.1 N 23.43 O. Found: 66.8 C 5.7 H 4.1 N 23.7 O.

EXAMPLE 98

3,4-Dimethyl-7-(3-cyclopentylisoxazol-5-yl)-methoxycoumarin

Yield: 56%; mp. 128° C. (methanol). $C_{19}H_{20}N_2O_4$ (340). Calculated: 67.05 C 5.92 H 8.23 N 18.89 O. Found: 66.9 C 6.0 H 8.1 N 18.9 O.

EXAMPLE 99

3,4-Dimethyl-7-(3-cyclohexylisoxazol-5-yl)-methoxycoumarin

Yield: 77%; mp. 143° C. $C_{20}H_{22}0N_2O_4$ (354). Calculated: 67.78 C 6.26 H 7.90 N 18.06 O. Found: 67.5 C 6.3 H 7.9 N 18.3 O.

EXAMPLE 100

6-Chloro-3,4-dimethyl-7-(2-pyridinyl)-methoxycoumarin

The procedure and working up were carried out as described under Example 2. In addition, 0.1% of 18-crown-6 was added to the reaction mixture.

Yield: 74%; mp. 201° C. (methanol). $C_{17}H_{14}CPNO_3$ (316). Calculated: 64.67 C 4.47 H 11.23 Cl 4.44 N 15.20 O. Found: 64.4 C 4.6 H 11.6 Cl 4.4 N 15.1 O.

EXAMPLE 101

3,6-Dichloro-4-methyl-7-(5-methyl-1,3,4-thiadiazol-2-yl)-methoxycoumarin

Yield: 19.5%; mp. 216° C. (methanol). $C_{14}H_{10}Cl_2N_2O_3S$ (357). Calculated: 47.07 C 2.82 H 19.85 Cl 7.84 N 13.44 O 8.98 S. Found: 46.9 C 2.9 H 19.4 Cl 7.8 N 13.7 O 8.9 S.

EXAMPLE 102

6-Bromo-3-chloro-4-methyl-7-(1-methyl-5-isopropyl-pyrazol-3-yl)-methoxycoumarin

The procedure and working up were carried out similarly to Example 100.

Yield: 46%; mp. 165° C. (methanol). $C_{18}H_{16}BrClN_2O_3$ (426). Calculated: 50.79 C 4.26 H 18.77 Br 8.33 Cl 6.58 N 11.27 O. Found: 50.2 C 4.1 H 18.4 Br 8.7 Cl 6.4 N 11.5 O.

EXAMPLE 103

3,6-Dichloro-4-methyl-7-(2-isopropylthiazol-4-yl)-methoxycoumarin

The procedure and working up were carried out similarly to Example 100.

Yield: 28% mp. 175° C. (methanol). $C_{17}H_{16}ClNO_3S$ (385). Calculated: 53.00 C 4.19 H 18.40 Cl 3.64 N 12.40 O 8.32 S. Found: 52.8 C 4.0 H 18.5 Cl 3.6 N 12.5 O 8.3 S.

EXAMPLE 104

6-Bromo-3-chloro-4-methyl-7-(2-isopropylthiazol-4-yl)-methoxycoumarin

The procedure and working up were carried out similarly to Example 100.

Yield: 22%; mp. 186° C. (methanol). $C_{17}H_{16}BrClNO_3S$ (428). Calculated: 47.60 C 3.50 H 18.60 Br 8.28 Cl 3.26 N 11.20 O 7.46 S. Found: 47.7 C 3.6 H 18.7 Br 8.4 Cl 3.2 N 11.30 O 7.5 S.

EXAMPLE 105

3,4-Dimethyl-7-(3-phenylisoxazol-5-yl)-methoxycoumarin

Yield: 73% mp. 186° C. (ethanol). $C_{21}H_{17}NO_4$ (347). Calculated: 72.61 C 4.93 H 4.03 N 18.42 O. Found: 72.6 C 5.1 H 3.9 N 18.4 O.

EXAMPLE 106

3,4-Dimethyl-7-(4-methyloxazol-5-yl)-methoxycoumarin

The procedure and working up were carried out similarly to Example 10.

Yield: 34% mp. 187° C. (methanol).

EXAMPLE 107

4-Trifluoromethyl-7-(2-methyl-1,3,4-thiadiazol-5-yl)-methoxycoumarin

The procedure and working up were carried out similarly to Example 10.

Yield: 76%; mp. 178° C. (methanol).

A) Tablets having the following composition were pressed on a tabletting press in a conventional manner:
- 40.00 mg of the substance of Example 108
- 120.00 mg of corn starch
- 13.50 mg of gelatine
- 45.00 mg of lactose
- 2.25 mg of Aerosil ® (chemically pure silica in the form of submicroscopic particles)
- 6.75 mg of potato starch (as 6% strength base)

B) 20.00 mg of the substance of Example 75
60.00 mg of core material

The core material consists of 9 parts of corn starch, 3 parts of lactose and 1 part of Luviskol ® VA 64 (60:40 vinylpyrrolidone/vinyl acetate copolymer, cf. Pharm. Ind. 1962, 586). The sugar-coating material consists of 5 parts of sucrose, 2 parts of corn starch, 2 parts of calcium carbonate and 1 part of talc. The coated tablets prepared in this manner are then provided with a coating which is resistant to gastric juice.

We claim:

1. An alkoxycoumarin substituted by a heterocyclic radical, of the formula

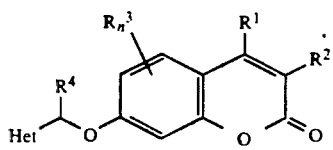

in which $R^1$ and $R^2$ independently of one another are each hydrogen, $C_1$-$C_5$-alkyl, trifluoromethyl, phenyl or halogen, or together form a $C_3$-$C_5$-alkylene chain, $R^3$ is $C_1$-$C_5$-alkyl or halogen, n is an integer of from 0 to 3, $R^4$ is hydrogen or $C_1$-$C_4$-alkyl and Het is

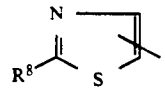

where $R^8$ is $C_1$-$C_5$-alkyl, $C_3$-$C_8$-cycloalkyl, benzyl or phenyl.

2. The heterocyclic-substituted alkoxycoumarin of claim 1 selected from the group consisting of:
3,6-Dichloro-4-methyl-7-(2-cyclopropylthiazol-4-yl)-methoxycoumarin,
3,4-Dimethyl-7-(2-methylthiazol-4-yl)-methoxycoumarin,
3,4-Dimethyl-7-(2-phenylthiazol-4-yl)-methoxycoumarin,
7-(2-Benzylthiazol-4-yl)-methoxy-3,4-dimethylcoumarin,
7-(2-Isopropylthiazol-4-yl)-methoxy-3,4-dimethylcoumarin,
7-(2-Cyclopropylthiazol-4-yl)-methoxy-3,4-dimethylcoumarin,
3,6-Dichloro-4-methyl-7-(2-isopropylthiazol-4-yl)-methoxycoumarin, and
6-Bromo-3-chloro-4-methyl-7-(2-isopropylthiazol-4yl)-methoxycoumarin.

3. The heterocyclic-substituted alkoxycoumarin of claim 2 which is 7-(2-Isopropylthiazol-4-yl)-methoxy-3,4-dimethylcoumarin.

4. An oral therapeutic agent which contains, as the active compound, from 10 to 500 mg, per dose, of an alkoxycoumarin substituted by a heterocyclic radical, of the formula

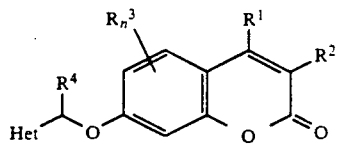

in which $R^1$ and $R^2$ independently of one another are each hydrogen, $C_1$-$C_5$-alkyl, trifluoromethyl, phenyl or halogen, or together form a $C_3$-$C_5$-alkylene chain, $R^3$ is $C_1$-$C_5$-alkyl or halogen, n is an integer of from 0 to 3, $R^4$ is hydrogen or $C_1$-$C_4$-alkyl and Het is

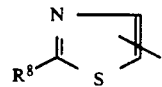

where $R^8$ is $C_1$-$C_5$-alkyl, $C_3$-$C_8$-cycloalkyl, benzyl or phenyl, in addition to conventional pharmaceutical auxiliaries.

5. A parenteral therapeutic agent which contains, as the active compound, from 1 to 50 mg, per dose, of an alkoxycoumarin substituted by a heterocyclic radical, of the formula

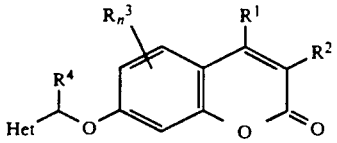

in which $R^1$ and $R^2$ independently of one another area each hydrogen, $C_1$-$C_5$-alkyl, trifluoromethyl, phenyl or halogen, or together form a $C_3$-$C_5$-alkylene chain, $R^3$ is $C_1$-$C_5$-alkyl or halogen, n is an integer of from 0 to 3, $R^4$ is hydrogen or $C_1$-$C_4$-alkyl and Het is

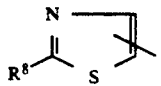

where $R^8$ is $C_1$-$C_5$-alkyl, $C_3$-$C_8$-cycloalkyl, benzyl or phenyl, in addition to conventional pharmaceutical auxiliaries.

6. An agent for treating neurodegenerative disorders caused by MAO activity which contains, as the active compound, an alkoxycoumarin substituted by a heterocyclic radical, of the formula

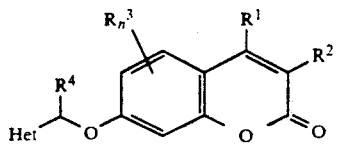  I in which $R^1$ and $R^2$ independently of one another are each hydrogen, $C_1$-$C_5$-alkyl, trifluoromethyl, phenyl or halogen, or together form a $C_3$-$C_5$-alkylene chain, $R^3$ is $C_1$-$C_5$-alkyl or halogen, n is an integer of from 0 to 3, $R^4$ is hydrogen or $C_1$-$C_4$-alkyl and Het is

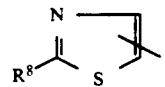

where $R^8$ is $C_1$-$C_5$-alkyl, $C_3$-$C_8$-cycloalkyl, benzyl or phenyl, in addition to conventional pharmaceutical auxiliaries.

7. A method for treating neurodegenerative disorders caused by MAO activity which comprises administering an effective amount of an alkoxycoumarin substituted by a heterocyclic radical, of the formula

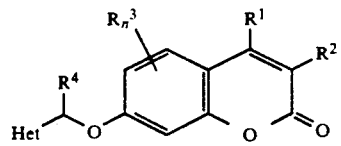  I in which $R^1$ and $R^2$ independently of one another are each hydrogen, $C_1$-$C_5$-alkyl, trifluoromethyl, phenyl or halogen, or together form a $C_3$-$C_5$-alkylene chain, $R^3$ is $C_1$-$C_5$-alkyl or halogen, n is an integer of from 0 to 3, $R^4$ is hydrogen or $C_1$-$C_4$-alkyl and Het is

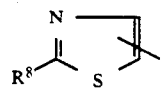

where $R^8$ is $C_1$-$C_5$-alkyl, $C_3$-$C_8$-cycloalkyl, benzyl or phenyl, to a human being or animal.

* * * * *